United States Patent
Kumar

(10) Patent No.: US 11,310,984 B2
(45) Date of Patent: Apr. 26, 2022

(54) MELON CULTIVARS ME466, ME467, ME468, ME469, ME470 AND ME480

(71) Applicant: SYNGENTA CROP PROTECTION AG, Basel (CH)

(72) Inventor: Rakesh Kumar, Woodland, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/802,681

(22) Filed: Feb. 27, 2020

(65) Prior Publication Data

US 2021/0267155 A1  Sep. 2, 2021

(51) Int. Cl.
*A01H 6/34* (2018.01)
*A01H 5/08* (2018.01)

(52) U.S. Cl.
CPC .............. *A01H 6/344* (2018.05); *A01H 5/08* (2013.01)

(58) Field of Classification Search
CPC combination set(s) only.
See application file for complete search history.

(56) References Cited

U.S. PATENT DOCUMENTS

| 8,618,361 | B1 | 12/2013 | Kumar et al. | |
| 8,878,013 | B1 | 11/2014 | Kumar et al. | |
| 9,596,813 | B1 | 3/2017 | Kumar | |
| 9,603,320 | B1 | 3/2017 | Kumar | |
| 2015/0156981 | A1* | 6/2015 | Humaydan | A01H 5/08 800/260 |
| 2020/0077613 | A1* | 3/2020 | Galea | A01H 6/344 |

OTHER PUBLICATIONS

PVP Certificate No. 9000077 for Muskmelon "Stephanie" dated Jun. 30, 1994.
Fresh Plaza.com Article "Aromatic netted Pregiato melons directly from Sicily," www.melonedoncamillo.it published May 22, 2013.

* cited by examiner

*Primary Examiner* — Brent T Page
(74) *Attorney, Agent, or Firm* — Karen A. Magri

(57) ABSTRACT

The present invention provides novel melon plants and plant parts, seed, fruit, and tissue culture therefrom. The invention also provides methods for producing a melon plant by crossing the melon plants of the invention with themselves or another melon plant. The invention also provides plants produced from such a crossing as well as plant parts, seed, fruit, and tissue culture therefrom.

35 Claims, No Drawings

MELON CULTIVARS ME466, ME467, ME468, ME469, ME470 AND ME480

FIELD OF THE INVENTION

This invention is in the field of melon plants, in particular, the invention relates to novel melon plants.

BACKGROUND OF THE INVENTION

Melons are found within the family Cucurbitaceae, which contains about 90 genera. Most of the melons consumed as fruit are within the genus *Cucumis*, with the vast majority belonging to the species *Cucumis melo* L. Cantaloupe is designated as *Cucumis melo* var. *cantalupensis*, and goes by a variety of common names including mushmelon, muskmelon, rockmelon, sweet melon and Persian melon.

Melons represent an important and valuable crop. Thus, there is an ongoing need for improved melon varieties having enhanced agronomic and/or consumer traits.

SUMMARY OF THE INVENTION

According to the invention, there is provided novel cantaloupe cultivars designated ME466, ME467, ME468, ME469, ME470 and ME480 characterized by a firm fruit flesh and extended shelf life. Thus, the invention also encompasses the seeds of cantaloupe cultivars ME466, ME467, ME468, ME469, ME470 and ME480, the plants of cantaloupe cultivars ME466, ME467, ME468, ME469, ME470 and ME480, parts of cantaloupe cultivars ME466, ME467, ME468, ME469, ME470 and ME480 (including fruit, seed, gametes, scion, rootstock, shoots), methods of producing seed from cantaloupe cultivars ME466, ME467, ME468, ME469, ME470 and ME480, and methods for producing a melon plant by crossing a cantaloupe of cultivar ME466, ME467, ME468, ME469, ME470 or ME480 with itself or another melon plant, methods for producing a melon plant comprising in its genetic material one or more transgenes, and the transgenic melon plants produced by that method. The invention also relates to methods for producing other melon plant derived from any of cantaloupe cultivars ME466, ME467, ME468, ME469, ME470 and ME480, and melon plants derived by the use of those methods. The present invention further relates to hybrid melon seed and plants (and parts thereof including fruit) produced by crossing any of cantaloupe cultivars ME466, ME467, ME468, ME469, ME470 and ME480 with another melon plant. In general, the plants and parts thereof of the invention are diploid plants and plant parts.

In another aspect, the present invention provides regenerable cells for use in tissue culture of cantaloupe cultivars ME466, ME467, ME468, ME469, ME470 and ME480. In representative embodiments, the tissue culture is capable of regenerating plants having essentially all of the physiological and morphological characteristics of the foregoing cantaloupe plants, and of regenerating plants having substantially the same genotype as the foregoing cantaloupe cultivars. Non-limiting examples of regenerable cells in such tissue cultures include meristematic cells, cotyledons, hypocotyl, leaves, pollen, embryos, roots, root tips, anthers, pistils, ovules, shoots, stems, petioles, pith, flowers, capsules, rootstock, scion and/or seeds as well as callus and/or protoplasts derived from any of the foregoing. Still further, the present invention provides plants regenerated from the tissue culture of the invention.

As a further aspect, the invention provides a method of producing melon seed, the method comprising crossing a plant of cantaloupe cultivar ME466, ME467, ME468, ME469, ME470 or ME480 with itself or a second melon plant. ME466, ME467, ME468, ME469, ME470 or ME480 can be the female and/or male parent. Optionally, the method further comprises collecting the seed.

The invention further provides a method of producing a progeny melon plant, the method comprising crossing a plant of cantaloupe cultivar ME466, ME467, ME468, ME469, ME470 or ME480 with itself or a second melon plant to produce at least a first progeny plant, which may optionally be a selfed plant or an F1 hybrid. ME466, ME467, ME468, ME469, ME470 or ME480 can be the female and/or male parent.

Another aspect of the invention provides methods for producing hybrids and other melon plants derived from cantaloupe cultivars ME466, ME467, ME468, ME469, ME470 and ME480. Melon plants derived by the use of those methods are also part of the invention as well as plant parts, (e.g., seed, gametes, fruit, scions, rootstock) and tissue culture from such hybrid or derived melon plants.

In representative embodiments, a melon plant derived from cantaloupe cultivar ME466, ME467, ME468, ME469, ME470 or ME480 comprises cells comprising at least one set of chromosomes derived from cantaloupe cultivar ME466, ME467, ME468, ME469, ME470 or ME480.

In embodiments, a melon plant or population of melon plants derived from cantaloupe cultivar ME466, ME467, ME468, ME469, ME470 or ME480 comprises, on average, at least about 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., theoretical allelic content; TAC) from cantaloupe cultivar ME466, ME467, ME468, ME469, ME470 or ME480, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of cantaloupe cultivar ME466, ME467, ME468, ME469, ME470 or ME480, and optionally may be the result of a breeding process comprising one or two breeding crosses and one or more of selfing, backcrossing and/or double haploid techniques in any combination and any order. In embodiments, the breeding process does not include a breeding cross, and comprises selfing, backcrossing and or double haploid technology. In embodiments, the melon plant derived from cantaloupe cultivar ME466, ME467, ME468, ME469, ME470 or ME480 is one, two, three, four, five or more breeding crosses removed from cantaloupe cultivar ME466, ME467, ME468, ME469, ME470 or ME480.

In embodiments, a hybrid or derived plant from cantaloupe cultivar ME466, ME467, ME468, ME469, ME470 or ME480 comprises a desired added trait(s). In representative embodiments, a melon plant derived from cantaloupe cultivar ME466, ME467, ME468, ME469, ME470 or ME480 comprises some or all of the morphological and physiological characteristics of cantaloupe cultivar ME466, ME467, ME468, ME469, ME470 or ME480 (e.g., as described herein, in particular, in Tables 1 to 3). In embodiments, the melon plant derived from cantaloupe cultivar ME466, ME467, ME468, ME469, ME470 or ME480 comprises essentially all of the morphological and physiological characteristics of cantaloupe cultivar ME466, ME467, ME468, ME469, ME470 or ME480 (e.g., as described herein, in particular, in Tables 1 to 3), with the addition of a desired added trait(s).

The invention also relates to methods for producing a melon plant comprising in its genetic material one or more transgenes and to the transgenic melon plant produced by those methods. Also provided are plant parts, seed, fruit and tissue culture from such transgenic melon plants, optionally wherein one or more cells in the plant part, seed, fruit or tissue culture comprise the transgene. The transgene can be introduced via plant transformation and/or breeding techniques.

In another aspect, the present invention provides for single locus converted plants of cantaloupe cultivars ME466, ME467, ME468, ME469, ME470 and ME480. Plant parts, seed, fruit and tissue culture from such single locus converted plants are also contemplated by the present invention. The single transferred locus may be a dominant or recessive allele. In illustrative embodiments, the single transferred locus will confer such traits as male sterility, male fertility, herbicide resistance, pest (e.g., insect and/or nematode) resistance, modified fatty acid metabolism, modified carbohydrate metabolism, disease resistance (e.g., for bacterial, fungal and/or viral disease), male fertility, enhanced nutritional quality, increased sweetness, increased flavor, improved ripening control, improved salt tolerance, improved appearance (e.g., fruit color), industrial usage or any combination thereof. The single locus may be a naturally occurring melon locus, a genome edited locus, a mutated locus (e.g., chemically or radiation induced), or a transgene introduced into melon through genetic engineering techniques.

The invention further provides methods for developing melon plants in a melon plant breeding program using plant breeding techniques including without limitation recurrent selection, backcrossing, pedigree breeding, mutation breeding, double haploid techniques, restriction fragment length polymorphism enhanced selection, genetic marker enhanced selection, and/or transformation. Seeds, melon plants, and parts thereof (including fruit), produced by such breeding methods are also part of the invention.

The invention also provides methods of multiplication or propagation of melon plants of the invention, which can be accomplished using any method known in the art, for example, via vegetative propagation and/or seed.

The invention further provides a method of producing food or feed comprising (a) obtaining a melon plant of the invention, wherein the plant has been cultivated to maturity, and (b) collecting a melon fruit from the plant.

Additional aspects of the invention include harvested products and processed products from the melon plants of the invention. A harvested product can be a whole plant or any plant part, as described herein. Thus, in some embodiments, a non-limiting example of a harvested product includes a seed or a fruit (or a part thereof including the flesh and/or rind), a rootstock, a scion, a shoot, a leaf, a stem, and the like.

In representative embodiments, a processed product includes, but is not limited to, cut, sliced, ground, pureed, dried, canned, jarred, packaged, frozen and/or heated fruit (including the flesh and/or rind) and/or seeds of the melon plants of the invention, or any other part thereof. In embodiments, a processed product includes a flour, meal, sauce, salad, or puree containing a plant of the invention, or a part thereof (e.g., the fruit and/or seed). In embodiments, the processed product includes washed and slice fruit (or parts thereof, e.g., the fruit flesh with or without the rind) of the invention.

The seed of the invention can optionally be provided as an essentially homogenous population of seed of a single plant or cultivar. Essentially homogenous populations of seed are generally free from substantial numbers of other seed, e.g., at least about 90%, 95%, 96%, 97%, 98% or 99% pure.

In representative embodiments, the invention provides a seed of a cantaloupe selected from cantaloupe cultivar ME466, ME467, ME468, ME469, ME470 or ME480.

As a further aspect, the invention provides a plant of cantaloupe cultivar ME466, ME467, ME468, ME469, ME470 or ME480.

As an additional aspect, the invention provides a cantaloupe plant, or a part thereof, having all the physiological and morphological characteristics of a plant of cantaloupe cultivar ME466, ME467, ME468, ME469, ME470 or ME480.

As another aspect, the invention provides fruit and/or seed of the melon plants of the invention and a processed product from the fruit (e.g., flesh with or without the rind) and/or seed of the inventive melon plants.

As still another aspect, the invention provides a method of producing cantaloupe seed, the method comprising crossing a melon plant of the invention with itself or a second melon plant. The invention also provides seed produced by this method and plants produced by growing the seed.

As yet a further aspect, the invention provides a method for producing a seed of a melon plant derived from cantaloupe cultivar ME466, ME467, ME468, ME469, ME470 or ME480, the method comprising: (a) crossing a melon plant of cantaloupe cultivar ME466, ME467, ME468, ME469, ME470 or ME480 with a second melon plant; and (b) allowing seed of a melon plant derived from cantaloupe ME466, ME467, ME468, ME469, ME470 or ME480 to form. In embodiments, the method further comprises: (c) growing a plant from the seed of step (b) to produce a plant derived from cantaloupe cultivar ME466, ME467, ME468, ME469, ME470 or ME480; (d) selfing the plant of step (c) or crossing it to a second melon plant to form additional melon seed derived from cantaloupe cultivar ME466, ME467, ME468, ME469, ME470 or ME480; and (e) optionally repeating steps (c) and (d) one or more times (e.g., one, two, one to three, one to five, one to six, one to seven, one to ten, three to five, three to six, three to seven, three to eight or three to ten times) to generate further derived melon seed from cantaloupe cultivar ME466, ME467, ME468, ME469, ME470 or ME480, wherein in step (c) a plant is grown from the additional melon seed of step (d) in place of growing a plant from the seed of step (b). In embodiments, the method comprises (e) repeating steps (c) and (d) one or more times (e.g., one to three, one to five, one to six, one to seven, one to ten, three to five, three to six, three to seven, three to eight or three to ten times) to generate further derived melon seed. As another option, in embodiments, the method comprises collecting the melon seed. The invention also provides seed produced by these methods and plants derived from cantaloupe cultivar ME466, ME467, ME468, ME469, ME470 or ME480 produced by growing the seed.

As another aspect, the invention provides a method of producing cantaloupe fruit, the method comprising: (a) growing cantaloupe cultivar ME466, ME467, ME468, ME469, ME470 or ME480; and (b) collecting fruit from the plant. The invention also provides the fruit produced by this method.

Still further, as another aspect, the invention provides a method of vegetatively propagating a plant of cantaloupe cultivar ME466, ME467, ME468, ME469, ME470 or ME480, the method comprising: (a) collecting tissue capable of being propagated from a plant of cantaloupe cultivar ME466, ME467, ME468, ME469, ME470 or ME480; (b) cultivating the tissue to obtain proliferated shoots; and (c) rooting the proliferated shoots to obtain rooted plantlets. Optionally, the invention further comprises growing plants from the rooted plantlets. The invention also encompasses the plantlets and plants produced by these methods.

As an additional aspect, the invention provides a method of producing a plant derived from cantaloupe cultivar ME466, ME467, ME468, ME469, ME470 or ME480 comprising a desired added trait, the method comprising: (a) crossing a first plant of cantaloupe cultivar ME466, ME467, ME468, ME469, ME470 or ME480 with a second melon plant that comprises a desired trait to produce F1 progeny; (b) selecting an F1 progeny that comprises the desired trait; (c) crossing the selected F1 progeny with the first plant of cantaloupe ME466, ME467, ME468, ME469, ME470 or ME480 to produce backcross progeny; and (d) selecting backcross progeny comprising the desired trait to produce a plant derived from cantaloupe ME466, ME467, ME468, ME469, ME470 or ME480 comprising a desired trait.

In embodiments, the selected progeny has a firm fruit flesh and/or extended shelf life. In embodiments, the selected progeny comprises all the morphological and physiological characteristics of the first plant of cantaloupe cultivar ME466, ME467, ME468, ME469, ME470 or ME480. Optionally, the method further comprises: (e) repeating steps (c) and (d) one or more times in succession (e.g., one to five, one to six, one to seven, one to ten, three to five, three to six, three to seven, three to eight or three to ten times) to produce a plant derived from cantaloupe cultivar ME466, ME467, ME468, ME469, ME470 or ME480 comprising a desired trait.

In representative embodiments, the invention also provides a method of producing a plant of cantaloupe ME466, ME467, ME468, ME469, ME470 or ME480 comprising a desired added trait, the method comprising introducing a transgene conferring the desired trait into a plant of cantaloupe ME466, ME467, ME468, ME469, ME470 or ME480. The transgene can be introduced by transformation methods (e.g., genetic engineering) or breeding techniques. Plants produced by the method and progeny thereof are also provided. In embodiments, the plant comprising the transgene produces a fruit with firm flesh and/or extended shelf life. In embodiments, a plant comprising the transgene comprises all the morphological and physiological characteristics of cantaloupe cultivar ME466, ME467, ME468, ME469, ME470 or ME480.

The invention also provides melon plants produced by the methods of the invention or a selfed progeny thereof, wherein the melon plant has the desired added trait as well as seed from such melon plants.

According to the foregoing methods, the desired added trait can be any suitable trait known in the art including, for example, male sterility, male fertility, herbicide resistance, pest (e.g., insect and/or nematode) resistance, modified fatty acid metabolism, modified carbohydrate metabolism, disease resistance (e.g., for bacterial, fungal and/or viral disease), enhanced nutritional quality, increased sweetness, increased flavor, improved ripening control, improved salt tolerance, improved appearance (e.g., fruit color) industrial usage, or any combination thereof).

In representative embodiments, a transgene conferring herbicide resistance confers resistance to glyphosate, sulfonylurea, imidazolinone, dicamba, glufosinate, phenoxy propionic acid, L-phosphinothricin, cyclohexone, cyclohexanedione, triazine, benzonitrile, or any combination thereof.

In representative embodiments, a transgene conferring pest resistance (e.g., insect and/or nematode) encodes a *Bacillus thuringiensis* endotoxin.

As a further embodiment, the invention provides a method for producing a seed of a melon plant derived from cantaloupe cultivars, the method comprising selfing a melon plant of cantaloupe cultivar ME469, ME470 or ME480 for one or more generations and allowing seed to form. Optionally, cantaloupe cultivar ME469, ME470 or ME480 is selfed for one, two, three, four, five, six, seven, eight, nine, ten or more generations. In embodiments, ME469, ME470 or ME480 is selfed for a sufficient number of generations to produce a substantially homozygous inbred line. Also provided is cantaloupe seed produced by the methods of the invention, optionally wherein the cantaloupe seed grows an inbred cantaloupe plant.

In representative embodiments, plants of the invention, including without limitation, transgenic plants, single locus converted plants, hybrid plants and melon plants derived from cantaloupe cultivars ME466, ME467, ME468, ME469, ME470 and ME480, are characterized, e.g., by producing a fruit with firm flesh and/or extended shelf life. In representative embodiments, plants of the invention, including without limitation, transgenic plants, single locus converted plants, hybrid plants and melon plants derived from cantaloupe cultivars ME466, ME467, ME468, ME469, ME470 or ME480, have at least 2, 3, 4, 5, 6, 7, 8, 9, 10 or more of the morphological and physiological characteristics of cantaloupe cultivars ME466, ME467, ME468, ME469, ME470 or ME480, respectively (e.g., as described in Tables 1 to 3), or even of all the morphological and physiological characteristics of cantaloupe cultivars ME466, ME467, ME468, ME469, ME470 or ME480, respectively, so that said plants are not significantly different for said traits than cantaloupe cultivar ME466, ME467, ME468, ME469, ME470 or ME480, respectively, as determined at the 5% significance level when grown in the same environmental conditions; optionally, with the presence of one or more desired additional traits (e.g., male sterility, disease resistance, pest or insect resistance, herbicide resistance, and the like).

The invention also encompasses plant parts, plant material, pollen, ovules, fruit and seed from the melon plants of the invention. The invention also provides seeds that produce the melon plants of the invention. Also provided is a tissue culture of regenerable cells from the melon plants of the invention, where optionally, the regenerable cells are: (a) embryos, meristem, leaves, pollen, cotyledons, hypocotyls, roots, root tips, anthers, flowers, pistils, ovules, seed, shoots, stems, stalks, petioles, pith and/or capsules; or (b) callus or protoplasts derived from the cells of (a). Further provided are melon plants regenerated from a tissue culture of the invention.

In still yet another aspect, the invention provides a method of determining a genetic characteristic of cantaloupe cultivars ME466, ME467, ME468, ME469, ME470 or ME480 or a progeny thereof using molecular genetic techniques, e.g., a method of determining a genotype of cantaloupe cultivars ME466, ME467, ME468, ME469, ME470 or ME480 or a progeny thereof. In embodiments, the method comprises detecting in the genome of a ME466, ME467, ME468, ME469, ME470 or ME480 plant, or a progeny plant thereof, at least a first polymorphism, e.g., comprises nucleic acid amplification and/or nucleic acid sequencing. To illustrate, in embodiments, the method comprises obtaining a sample of nucleic acids from the plant and detecting at least a first polymorphism in the nucleic acid sample. Optionally, the method may comprise detecting a plurality of polymorphisms (e.g., two or more, three or more, four or more, five or more, six or more, eight or more or ten or more polymorphisms, etc.) in the genome of the plant. In representative embodiments, the method further comprises storing the results of the step of detecting the polymorphism(s) on a computer readable medium. The invention further provides a computer readable medium produced by such a method.

These and other aspects of the present invention are set forth in the detailed description of the invention below.

DETAILED DESCRIPTION OF THE INVENTION

The present invention is based, in part, on the development of novel melon cultivars having desirable characteristics including fruit with firm flesh and an extended shelf life.

It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features and embodiments of the invention described herein can be used in any combination.

Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

I. Definitions

In the description and tables which follow, a number of terms are used. In order to provide a clear and consistent understanding of the specification and claims, including the scope to be given such terms, the following definitions are provided:

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of ±20%, ±10%, ±5%, ±1%, ±0.5%, or even ±0.1% of the specified amount.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" when used in a claim or the description of this invention is not intended to be interpreted to be equivalent to "comprising."

"Allele". An allele is any of one or more alternative forms of a gene, all of which relate to a trait or characteristic. In a diploid cell or organism, the two alleles of a given gene occupy corresponding loci on a pair of homologous chromosomes.

"Backcrossing". Backcrossing is a process in which a breeder repeatedly crosses hybrid progeny back to one of the parents, for example, a first generation hybrid F1 with one of the parental genotype of the F1 hybrid.

"Cotyledon". One of the first leaves of the embryo of a seed plant; typically one or more in monocotyledons, two in dicotyledons, and two or more in gymnosperms.

"Double haploid line". A stable inbred line achieved by doubling the chromosomes of a haploid line, e.g., from anther culture. For example, some pollen grains (haploid) cultivated under specific conditions develop plantlets containing 1 n chromosomes. The chromosomes in these plantlets are then induced to "double" (e.g., using chemical means) resulting in cells containing 2n chromosomes. The progeny of these plantlets are termed "double haploid" and are essentially non-segregating (e.g., are stable). The term "double haploid" is used interchangeably herein with "dihaploid."

"Essentially all the physiological and morphological characteristics". A plant having "essentially all the physiological and morphological characteristics" (and similar phrases) means a plant having all of the desired physiological and morphological characteristics of the recurrent parent, except for the characteristic(s) derived from the converted locus/loci (e.g., a single converted locus), for example, introduced via backcrossing to a cantaloupe cultivar of the invention, a modified gene(s) resulting from genome editing techniques, an introduced transgene (i.e., introduced via genetic transformation techniques or mutation (e.g., chemical or radiation induced), when both plants are grown under the same environmental conditions. In embodiments, a plant having "essentially all of the physiological and morphological characteristics" means a plant having all of the characteristics of the reference plant with the exception of five or fewer traits, four or fewer traits, three or fewer traits, two or fewer traits, or one trait. In embodiments, the plant comprising "essentially all of the physiological and morphological characteristics of variety ME466, ME467, ME468, ME469, ME470 or ME480 produces fruits with a firm flesh and extended shelf life. In embodiments, a plant having "essentially all of the physiological and morphological characteristics" of variety ME466, ME467, ME468, ME469, ME470 or ME480 comprises the traits of Tables 1 to 3.

"Gene". As used herein, "gene" refers to a segment of nucleic acid comprising an open reading frame. A gene can be introduced into a genome of a species, whether from a different species or from the same species, using transformation or various breeding methods.

"Inbred line". As used herein, the phrase "inbred line" refers to a genetically homozygous or nearly homozygous population. An inbred line, for example, can be derived through several cycles of sib crossing and/or selfing and/or via double haploid production. In some embodiments, inbred lines breed true for one or more traits of interest. An "inbred plant" or "inbred progeny" is an individual sampled from an inbred line.

"Plant." As used herein, the term "plant" includes plant cells, plant protoplasts, plant cell tissue cultures from which plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, fruit, stems, rootstocks, scions, and the like.

"Plant material". The terms "plant material" and "material obtainable from a plant" are used interchangeably herein and refer to any plant material obtainable from a plant including without limitation, leaves, stems, roots, flowers or flower parts, fruits, pollen, egg cells, zygotes, seeds, cuttings, cell or tissue cultures, rootstocks, scions, or any other part or product of the plant.

"Plant part". As used herein, a "plant part" includes any part, organ, tissue or cell of a plant including without limitation an embryo, meristem, leaf, pollen, cotyledon, hypocotyl, root, root tip, anther, flower, flower bud, pistil, ovule, seed, shoot, stem, stalk, petiole, pith, capsule, a scion, a rootstock and/or a fruit including callus and protoplasts derived from any of the foregoing.

"Quantitative Trait Loci". Quantitative Trait Loci (QTL) refers to genetic loci that control to some degree, numerically representable traits that are usually continuously distributed.

"Regeneration". Regeneration refers to the development of a plant from tissue culture.

"Resistance". As used herein the terms "resistance" and "tolerance" (and grammatical variations thereof) are used interchangeably to describe plants that show reduced or essentially no symptoms to a specific biotic (e.g., a pest, pathogen or disease) or abiotic (e.g., exogenous or environmental, including herbicides) factor or stressor. In some embodiments, "resistant" or "tolerant" plants show some symptoms but are still able to produce marketable product with an acceptable yield, e.g., the yield may still be reduced and/or the plants may be stunted as compared with the yield or growth in the absence of the biotic and/or abiotic factor or stressor. Those skilled in the art will appreciate that the degree of resistance or tolerance may be assessed with respect to a plurality or even an entire field of plants. A melon plant may be considered "resistant" or "tolerant" if resistance/tolerance is observed over a plurality of plants (e.g., an average), even if particular individual plants may be susceptible to the biotic or abiotic factor or stressor.

"RHS". RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

"Single locus converted". A single locus converted or conversion plant refers to a plant that is developed by plant breeding techniques (e.g., backcrossing), genome editing techniques, genetic transformation techniques and/or mutation techniques (e.g., chemical or radiation induced) wherein essentially all of the desired morphological and physiological characteristics of a line are recovered in addition to the single locus introduced into the line via the plant breeding, genome editing, genetic transformation or mutation techniques.

"Substantially equivalent characteristic". A characteristic that, when compared, does not show a statistically significant difference (e.g., p=0.05) from the mean.

"Transgene". A nucleic acid of interest that can be introduced into the genome of a plant by genetic engineering techniques (e.g., transformation) or breeding. The transgene can be from the same or a different species. If from the same species, the transgene can be an additional copy of a native coding sequence or can present the native sequence in a form or context (e.g., different genomic location and/or in operable association with exogenous regulatory elements such as a promoter) than is found in the native state. The transgene can encode a polypeptide or a functional non-translated RNA (e.g., RNAi).

Botanical Description of the Novel Melon Plants of the Invention.

In representative embodiments, the melon plants of the invention are characterized by producing fruits with a firm flesh and extended shelf life. For example, in embodiments, the melon plants of the invention produce a fruit having at maturity a flesh firmness of at least about 5, 5.5, 6, 6.5, 7 or 7.5 pound force (e.g., when measured with a FT011 penetrometer with an 8 mm probe size). One exemplary method for measuring flesh firmness is to insert the tip of a penetrometer into the flesh of the melon up to about 0.5 inches deep. Multiple measurements at different sites (e.g., three measurements/sites) in the fruit can be made to determine an average flesh firmness. In general, a traditional western shipper cantaloupe has a mature flesh firmness of about 4 pound force.

Those skilled in the art will appreciate that cantaloupe plants can be readily crossed with other melons, e.g., another *C. melo* melon including without limitation, honeydew, Tuscan, Piel de Sapo, Yellow Canary, Japanese, Charentais, Galia, Amarello, Kirkagak, Hamy, Ananas, Oriental, and the like. Thus, the melon plants of the invention encompass hybrid melon plants arising from crosses between cantaloupe cultivar ME466, ME467, ME468, ME469, ME470 or ME480 and another melon plant (cantaloupe or other melon), as well as melon plants derived from cantaloupe cultivar ME466, ME467, ME468, ME469, ME470 or ME480 that have a lineage including any of cantaloupe cultivar ME466, ME467, ME468, ME469, ME470 or ME480 and another melon plant (cantaloupe or other melon type).

Botanical descriptions of cantaloupe varieties ME466, ME467, ME468, ME469, ME470 and ME480 are provided below.

Lines ME466, ME467 and ME468.

Breeding methods. Melon lines ME466, ME467 and ME468 are sister lines that were developed by the single seed descent method of breeding. Based on observations in a large number of plants in the last generation, ME466, ME467 and ME468 are each unique, genetically stable, and phenotypically uniform. No variants have been observed in the population of ME466, ME467 and ME468, and no genetic variations are expected in these lines.

Hybrid production. Test crosses have been made with ME466, ME467 and ME468 as the female parent, and a number of promising hybrids have been identified (e.g., ME469, ME470, and ME480, all disclosed herein).

Further description of ME466, ME467 and ME468 and comparison are provided in Table 1.

TABLE 1

Morphological and Physiological Characteristics of Lines ME466, ME467 and ME468 (as observed in the field in Woodland, California, summer season 2019).

| Descriptor | Line ME466 | Line ME467 | Line ME468 |
|---|---|---|---|
| Type | Common or Summer | Common or Summer | Common or Summer |
| Area of best adaptation in U.S. | Southwest | Southwest | Southwest |
| Maturity (days from seeding to harvest) | 70 | 70 | 70 |
| Plant: | | | |
| Fertility | Monoecious | Monoecious | Monoecious |
| Habit | Vine | Vine | Vine |
| Leaf (mature blade of third leaf): | | | |
| Shape | Reniform | Reniform | Reniform |
| Lobes | Deeply lobed | Deeply lobed | Deeply lobed |
| Color | Medium Green (RHS 143A) | Medium Green (RHS 143A) | Medium Green (RHS 143A) |
| Length (mm) | 28 | 35.3 | 28 |
| Width (mm) | 40 | 48.7 | 41 |
| Surface | Pubescent | Pubescent | Pubescent |
| Fruit (at edible maturity): | | | |
| Length (cm) | 17 | 17.8 | 18.5 |
| Diameter (cm) | 17.6 | 17.2 | 17.8 |
| Shape | Round | Round | Oval |
| Surface | Netted | Netted | Netted |
| Blossom scar | Conspicuous | Conspicuous | Conspicuous |
| Rib presence | Absent | Absent | Present |
| No. of ribs per fruit | N/A | N/A | 9 |
| Shipping quality | Fair (short distance shipping) | Fair (short distance shipping) | Fair (short distance shipping) |
| Fruit abscission | When ripe | When ripe | When ripe |
| Rind net: | | | |
| Net presence | Sparse | Sparse | Sparse |
| Distribution | Covers entire fruit | Covers entire fruit | Covers entire fruit |
| Coarseness | Medium coarse | Medium coarse | Medium coarse |
| Interlacing | Complete | Complete | Complete |
| Interstices | Shallow | Shallow | Medium deep |
| Rind color at edible maturity: | | | |
| Primary color | Yellow (RHS 15A) | Yellow (RHS 15A) | Yellow (RHS 15A) |
| Flesh at edible maturity: | | | |
| Color near cavity | Orange (RHS 25B) | Orange (RHS 25B) | Orange (RHS 25B) |
| Color in center | Orange (RHS 25B) | Orange (RHS 25B) | Orange (RHS 25B) |
| Color near rind | Orange (RHS 25A) | Orange (RHS 25A) | Orange (RHS 25B) |
| Refractometer % soluble solids (center of flesh) | 12 | 12 | 12 |
| Aroma | Strong | Strong | Strong |
| Flavor | Somewhat spicy | Somewhat spicy | Somewhat spicy |
| Seed cavity: | | | |
| Length (mm) | 54.5 | 63 | 64.5 |
| Width (mm) | 61.5 | 57 | 61 |
| Shape in X-section | Triangular | Triangular | Triangular |
| Seeds: | | | |
| Grams per 1000 seeds | 30 | 30 | 30 |

Hybrids ME469, ME470 and ME480.

Hybrid ME469 (also designated as Garth) was developed by crossing line ME467 (disclosed herein) as a female and proprietary inbred cantaloupe line ME378 as a male parent.

Hybrid ME470 (also designated as Desert Express) was developed by crossing line ME466 (disclosed herein) as a female and proprietary inbred cantaloupe line ME378 as a male parent.

Hybrid ME480 (also designated as ME7587) was developed by crossing line ME468 (disclosed herein) as a female and proprietary inbred cantaloupe line ME378 as a male parent.

The F1 hybrids ME469, ME470 and ME480 are stable for most phenotypic traits such as fruit size and shape, uniformity, flesh firmness and total soluble solids, within the limits of environmental influence.

As compared with melon hybrid Sweet Spring (ME356; U.S. Pat. No. 9,596,813 B1), hybrids ME469, ME470 and ME480 have a flesh firmness of 7 pounds-force using a fruit penetrometer with an 8 mm probe, whereas the fruit of Sweet Spring has a firmness of 6 pounds-force.

Further description of hybrids ME469, ME470 and ME480 are provided in Table 2.

TABLE 2

Morphological and Physiological Characteristics of hybrids ME469 ME470 and ME480 (as observed in the field in Woodland, California, summer season 2019).

| Descriptor | Hybrid ME469 | Hybrid ME470 | Hybrid ME480 |
|---|---|---|---|
| Type | Common or Summer | Common or Summer | Common or Summer |
| Area of best adaptation in U.S. | Southwest | Southwest | Southwest |
| Maturity (days from seeding to harvest) | 70 | 70 | 70 |
| Plant: | | | |
| Fertility | Monoecious | Monoecious | Andromonoecious |
| Habit | Vine | Vine | Vine |
| Leaf (mature blade of third leaf): | | | |
| Shape | Reniform | Reniform | Reniform |
| Lobes | Deeply lobed | Deeply lobed | Deeply lobed |
| Color | Medium Green (RHS 143A) | Medium Green (RHS 143A) | Medium Green (RHS 143A) |
| Length (mm) | 29 | 39 | 32.7 |
| Width (mm) | 41.3 | 52.7 | 43.3 |
| Surface | Pubescent | Pubescent | Pubescent |
| Fruit (at edible maturity): | | | |
| Length (cm) | 17.8 | 16.7 | 18.1 |
| Diameter (cm) | 14.8 | 16 | 16.4 |
| Shape | Round oval | Round oval | Round oval |
| Surface | Netted | Netted | Netted |
| Blossom scar | Conspicuous | Conspicuous | Conspicuous |
| Rib presence | Absent | Absent | Absent |
| Shipping quality | Fair (short distance shipping) | Fair (short distance shipping) | Fair (short distance shipping) |
| Fruit abscission | When ripe | When ripe | When ripe |
| Rind net: | | | |
| Net presence | Abundant | Abundant | Abundant |
| Distribution | Covers entire fruit | Covers entire fruit | Covers entire fruit |
| Coarseness | Very coarse | Very coarse | Very coarse |
| Interlacing | Complete | Complete | Complete |
| Interstices | Medium deep | Medium deep | Medium deep |
| Rind texture: | | | |
| Texture | Firm | Firm | Firm |
| Rind color at edible maturity: | | | |
| Primary color | Yellow (RHS 15A) | Yellow (RHS 15A) | Yellow (RHS 15A) |
| Flesh at edible maturity: | | | |
| Color near cavity | Orange (RHS 25B) | Orange (RHS 25C) | Orange (RHS 25B) |
| Color in center | Orange (RHS 25C) | Orange (RHS 25B) | Orange (RHS 25B) |
| Color near rind | Orange (RHS 25A) | Orange (RHS 25A) | Orange (RHS 25B) |
| Refractometer % soluble solids (center of flesh) | 13 | 13 | 13 |
| Aroma | Strong | Strong | Strong |
| Flavor | Somewhat spicy | Somewhat spicy | Somewhat spicy |
| Seed cavity: | | | |
| Length (mm) | 57.5 | 68 | 66 |
| Width (mm) | 63.5 | 71 | 72 |
| Shape in X-section | Triangular | Triangular | Triangular |
| Disease resistance: | | | |
| Powdery mildew | Resistant | Resistant | Resistant |
| Sulphur burn | Resistant | Resistant | Resistant |
| Fusarium wilt | Resistant | Resistant | Resistant |

Hybrids ME469, ME470 and ME480 were also evaluated in the field in Arizona. The results are shown in Table 3 below.

TABLE 3

| Descriptor | Hybrid ME469 | Hybrid ME470 | Hybrid ME480 |
|---|---|---|---|
| Plant vigor | 7 | 7 | 7 |
| Size 6 (%) | 22 | 15 | 10 |
| Size 9 (%) | 30 | 30 | 30 |
| Size 12 (%) | 32 | 35 | 40 |
| Size 15 (%) | 15 | 20 | 20 |
| Shape | Round oval | Round oval | Round oval |
| Fruit netting | 7 | 7 | 7 |
| Flesh color intensity | 9 | 9 | 9 |
| Seed cavity | 8.5 | 9 | 9 |
| Flesh firmness (lb) | 7 | 7 | 7 |
| Total soluble solids (Brix) | 14.2 | 14.6 | 14.6 |

| | | |
|---|---|---|
| Fruit netting: | 1 to 9 scale | Very dense = 9, less dense = 1 |
| Plant vigor: | 1 to 9 scale | Very strong = 9, weak = 1 |
| Flesh color intensity: | 1 to 9 scale | Dark orange = 9, pale = 1 |
| Fruit cavity: | 1 to 9 scale | Tightly closed = 9, very open = 1 |
| Total soluble solids: | °Brix | Total soluble solids of 10 typical fruit |
| Flesh firmness: | lb | Fruit flesh pressure in lbs of 10 typical fruit using 8 mm probe |
| Size 6: | % | Percent of fruit size 6 fruit per box. Fruit diameter of fruit: 17.0 cm > 6 size > 15.8 cm. |
| Size 9: | % | Percent of fruit size 9 fruit per box. Fruit diameter of fruit: 15.8 cm > 9 size > 14.6 cm. |
| Size 12: | % | Percent of fruit size 12 fruit per box. Fruit diameter of fruit: 14.6 cm > 12 size > 13.4 cm. |
| Size 15: | % | Percent of fruit size 15 fruit per box. Fruit diameter of fruit: 13.4 cm > 15 size > 12.6 cm. |

Tissue Culture.

In embodiments, melon plants can be propagated by tissue culture and regeneration. Tissue culture of various tissues of melon and regeneration of plants therefrom is well known and widely published. For example, reference may be had to Teng, et al., HortScience, 27:9, 1030-1032 (1992); Teng, et al., HortScience, 28:6, 669-1671 (1993); Zhang, et al., Journal of Genetics and Breeding, 46:3, 287-290 (1992); Webb, et al., Plant Cell Tissue and Organ Culture, 38:1, 77-79 (1994); Curtis, et al., Journal of Experimental Botany, 45:279, 1441-1449 (1994); Nagata, et al., Journal for the American Society for Horticultural Science, 125:6, 669-672 (2000); and Ibrahim, et al., Plant Cell Tissue and Organ Culture, 28(2), 139-145 (1992). It is clear from the literature that the state of the art is such that these methods of obtaining plants are routinely used and have a very high rate of success. Thus, another aspect of this invention is to provide cells which upon growth and differentiation produce melon plants having desired characteristics of cantaloupe cultivars ME466, ME467, ME468, ME469, ME470 and ME480 (e.g., a fruit with firm flesh and/or extended shelf life). Optionally, melon plants can be regenerated from the tissue culture of the invention comprising all the physiological and morphological characteristics of cantaloupe cultivars ME466, ME467, ME468, ME469, ME470 or ME480.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques.

Additional Breeding Methods.

This invention is also directed to methods for producing a melon plant by crossing a first parent melon plant with a second parent melon plant wherein the first or second parent melon plant is a plant of cantaloupe cultivar ME466, ME467, ME468, ME469, ME470 or ME480. Further, both first and second parent melon plants are a plant of cantaloupe cultivar ME466, ME467, ME468, ME469, ME470 or ME480. Thus, any of the following exemplary methods using cantaloupe cultivar ME466, ME467, ME468, ME469, ME470 or ME480 are part of this invention: selfing, backcrosses, double haploid technology, hybrid production, crosses to populations, and the like. All plants produced using cantaloupe cultivar ME466, ME467, ME468, ME469, ME470 or ME480 as at least one parent are within the scope of this invention, including those developed from melon plants derived from cantaloupe cultivar ME466, ME467, ME468, ME469, ME470 or ME480. Advantageously, cantaloupe cultivars ME466, ME467, ME468, ME469, ME470 and ME480 can be used in crosses with other, different, melon plants to produce first generation ($F_1$) melon hybrid seeds and plants with desirable characteristics. The cultivars of the invention can also be used for transformation where exogenous transgenes are introduced and expressed by the cultivars of the invention. Genetic variants created either through traditional breeding methods or through transformation of the cultivars of the invention by any of a number of protocols known to those of skill in the art are intended to be within the scope of this invention.

Those skilled in the art will appreciate that cantaloupe melons can be readily crossed with other melons, e.g., another *C. melo* melon including without limitation honeydew, Tuscan, Piel de Sapo, Yellow Canary, Japanese, Charentais, Galia, Amarello, Kirkagak, Hamy, Ananas, Oriental, and the like. Thus, the methods of the invention encompass crosses between cantaloupe cultivars ME466, ME467, ME468, ME469, ME470 and ME480, and progeny and derivatives thereof, with other melons including cantaloupe melons or any other melon type.

The following describes exemplary breeding methods that may be used with cantaloupe cultivar ME466, ME467, ME468, ME469, ME470 and ME480 in the development of further melon plants. One such embodiment is a method for developing cantaloupe cultivar ME466, ME467, ME468, ME469, ME470 and ME480 progeny melon plants in a melon plant breeding program comprising: obtaining a plant, or a part thereof, of cantaloupe cultivar ME466, ME467, ME468, ME469, ME470 or ME480, utilizing said plant or plant part as a source of breeding material, and selecting a cantaloupe cultivar ME466, ME467, ME468, ME469, ME470 or ME480 progeny plant with molecular markers in common with cantaloupe cultivar ME466, ME467, ME468, ME469, ME470 or ME480 and/or with morphological and/or physiological characteristics described herein (e.g., a fruit with firm flesh and/or extended shelf life). In representative embodiments, the progeny plant has at least 2, 3, 4, 5, 6, 7, 8, 9, 10 or more of the morphological and physiological characteristics of cantaloupe cultivars ME466, ME467, ME468, ME469, ME470 or ME480, respectively (e.g., as described in Tables 1 to 3), or even of all the morphological and physiological characteristics of cantaloupe cultivars ME466, ME467, ME468, ME469, ME470 or ME480, respectively, so that said progeny melon plant is not significantly different for said traits than cantaloupe cultivar ME466, ME467, ME468, ME469, ME470 or ME480, respectively, as determined at the 5% significance level when grown in the same environmental conditions; optionally, with the presence of one or more desired additional traits (e.g., male sterility, disease resistance, pest or insect resistance, herbicide resistance, and the like). Breeding steps that may be used in the breeding program include pedigree breeding, backcrossing, mutation breeding, and recurrent selection. In conjunction with these steps, techniques such as RFLP-enhanced selection, genetic marker enhanced selection (for example, SNP or SSR markers), and the making of double haploids may be utilized.

Another representative method involves producing a population of cantaloupe cultivar ME466, ME467, ME468, ME469, ME470 or ME480 progeny melon plants, comprising crossing a cantaloupe cultivar of the invention with another melon plant, thereby producing a population of melon plants, which, on average, derive 50% of their alleles from cantaloupe cultivar ME466, ME467, ME468, ME469, ME470 or ME480, respectively. A plant of this population may be selected and repeatedly selfed or sibbed with a melon plant resulting from these successive filial generations or backcrossed to cantaloupe cultivar ME466, ME467, ME468, ME469, ME470 or ME480. Another approach is to make double haploid plants to achieve homozygosity. One embodiment of this invention is a melon plant produced by these methods and that has obtained at least 50% of its alleles from cantaloupe cultivar ME466, ME467, ME468, ME469, ME470 or ME480. In embodiments, the methods of the invention produce a population of melon plants that, on average, derives at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from cantaloupe cultivar ME466, ME467, ME468, ME469, ME470 or ME480, e.g., at least about 6.25%, 12.5%, 25%, 30%, 35%, 40%, 45%, 50%, 55%, 60%, 65%, 70%, 75%, 80%, 85%, 90%, 95%, 96%, 97%, 98% or 99% of the genetic complement of cantaloupe cultivar ME466, ME467, ME468, ME469, ME470 or ME480. One representative embodiment of this invention is the melon plant produced by this method and that has obtained at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from cantaloupe cultivar ME466, ME467, ME468, ME469, ME470 or ME480, and optionally may be the result of a breeding process comprising one or two breeding crosses and one or more of selfing, sibbing, backcrossing and/or double haploid techniques in any combination and any order. In embodiments, the breeding process does not include a breeding cross, and comprises selfing, sibbing, backcrossing and/or double haploid technology.

One of ordinary skill in the art of plant breeding would know how to evaluate the traits of two plant varieties to determine if there is no significant difference between the two traits expressed by those varieties. For example, see Fehr and Walt, Principles of Cultivar Development, pp. 261-286 (1987). Thus, the invention includes cantaloupe cultivar ME466, ME467, ME468, ME469, ME470 or ME480 progeny melon plants characterized by producing fruit with firm flesh and/or an extended shelf life. In embodiments, the invention encompasses progeny plants having a combination of at least 2, 3, 4, 5 or 6 characteristics as described herein for cantaloupe cultivar ME466, ME467, ME468, ME469, ME470 or ME480, so that said progeny melon plant is not significantly different for said traits than cantaloupe cultivar ME466, ME467, ME468, ME469, ME470 or ME480, respectively, as determined at the 5% significance level when grown in the same environmental conditions. Using techniques described herein and those known in the art, molecular markers may be used to identify said progeny plant as progeny of cantaloupe cultivar ME466, ME467, ME468, ME469, ME470 and ME480. Mean trait values may be used to determine whether trait differences are significant, and optionally the traits are measured on plants grown under the same environmental conditions.

Progeny of cantaloupe cultivar ME466, ME467, ME468, ME469, ME470 and ME480 may also be characterized through their filial relationship with cantaloupe cultivar ME466, ME467, ME468, ME469, ME470 and ME480, respectively, as for example, being within a certain number of breeding crosses of cantaloupe cultivar ME466, ME467, ME468, ME469, ME470 and ME480. A breeding cross is a cross made to introduce new genetics into the progeny, and is distinguished from a cross, such as a self or a sib cross, made to select among existing genetic alleles. The lower the number of breeding crosses in the pedigree, the closer the relationship between cantaloupe cultivars ME466, ME467, ME468, ME469, ME470 or ME480 and its progeny. For example, progeny produced by the methods described herein may be within 1, 2, 3, 4, 5 or more breeding crosses of cantaloupe cultivars ME466, ME467, ME468, ME469, ME470 or ME480.

In representative embodiments, a melon plant derived from cantaloupe cultivars ME466, ME467, ME468, ME469, ME470 or ME480 comprises cells comprising at least one set of chromosomes derived from cantaloupe cultivars ME466, ME467, ME468, ME469, ME470 or ME480.

In embodiments, the melon plant or population of melon plants derived from cantaloupe cultivars ME466, ME467, ME468, ME469, ME470 or ME480 comprises, on average, at least 6.25%, 12.5%, 25%, 30%, 35%, 40%, 45%, 50%, 55%, 60%, 65%, 70%, 75%, 80%, 85%, 90%, 95%, 96%, 97%, 98% or 99% of its alleles (i.e., TAC) from cantaloupe cultivars ME466, ME467, ME468, ME469, ME470 or ME480, e.g., at least 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of cantaloupe cultivars ME466, ME467, ME468, ME469, ME470 or ME480, and optionally may be the result of one or more of selfing, sibbing, backcrossing and/or double haploid techniques in any combination and any order. In embodiments, the breeding process does not include a breeding cross, and comprises selfing, backcrossing and/or double haploid technology.

In embodiments, the melon plant derived from cantaloupe cultivars ME466, ME467, ME468, ME469, ME470 or ME480 is one, two, three, four, five or more breeding crosses removed from cantaloupe cultivars ME466, ME467, ME468, ME469, ME470 or ME480. In embodiments, the melon plant derived from cantaloupe cultivars ME466, ME467, ME468, ME469, ME470 or ME480 is two or less, three or less, four or less, or five or less breeding crosses removed from cantaloupe cultivars ME466, ME467, ME468, ME469, ME470 or ME480.

In representative embodiments, a plant derived from cantaloupe cultivars ME466, ME467, ME468, ME469, ME470 or ME480 is a double haploid plant, a hybrid plant or an inbred plant.

In embodiments, a hybrid or derived plant from cantaloupe cultivars ME466, ME467, ME468, ME469, ME470 or ME480 comprises a desired added trait. In representative embodiments, a melon plant derived from cantaloupe cultivars ME466, ME467, ME468, ME469, ME470 or ME480 comprises all of the morphological and physiological characteristics of cantaloupe cultivars ME466, ME467, ME468, ME469, ME470 or ME480 (e.g., as described herein, in particular, in Tables 1 to 3). In embodiments, the melon plant derived from cantaloupe cultivars ME466, ME467, ME468, ME469, ME470 or ME480 comprises all or essentially all of the morphological and physiological characteristics of cantaloupe cultivars ME466, ME467, ME468, ME469, ME470 or ME480 (e.g., as described herein, in particular, in Tables 1 to 3), with the addition of a desired added trait.

Genetic Transformation.

With the advent of molecular biological techniques that have allowed the isolation and characterization of genes that encode specific protein products, scientists in the field of plant biology developed a strong interest in engineering the genome of plants to contain and express foreign nucleic acids including additional or modified versions of native (endogenous) nucleic acids (optionally driven by a non-native promoter) in order to alter the traits of a plant in a specific manner. Any nucleic acid sequences, whether from a different species, the same species or an artificial sequence, which are introduced into the genome using transformation or various breeding methods, are referred to herein collectively as "transgenes." Over the last fifteen to twenty years, several methods for producing transgenic plants have been developed, and in particular embodiments the present invention also relates to transformed versions of melon plants disclosed herein.

Genetic engineering techniques can be used (alone or in combination with breeding methods) to introduce one or more desired added traits into plant, for example, cantaloupe cultivars ME466, ME467, ME468, ME469, ME470 or ME480 or progeny or melon plants derived thereof. Once a transgene has been introduction into a plant by genetic transformation, it can be transferred to other plants via conventional breeding.

Plant transformation generally involves the construction of an expression vector that will function in plant cells. Optionally, such a vector comprises one or more nucleic acids comprising a coding sequence for a polypeptide or an untranslated functional RNA under control of, or operatively linked to, a regulatory element (for example, a promoter). In representative embodiments, the vector(s) may be in the form of a plasmid, and can be used alone or in combination with other plasmids, to provide transformed melon plants using transformation methods as described herein to incorporate transgenes into the genetic material of the melon plant.

Additional methods include, but are not limited to, expression vectors introduced into plant tissues using a direct nucleic acid transfer method, such as microprojectile-mediated delivery (e.g., with a biolistic device), DNA injection, *Agrobacterium*-mediated transformation, electroporation, and the like. Transformed plants obtained from the plants (and parts and tissue culture thereof) of the invention are intended to be within the scope of this invention.

Expression Vectors for Plant Transformation—Selectable Markers.

Expression vectors typically include at least one nucleic acid comprising or encoding a selectable marker, operably linked to a regulatory element (for example, a promoter) that allows transformed cells containing the marker to be either recovered by negative selection, e.g., inhibiting growth of cells that do not contain the selectable marker, or by positive selection, e.g., screening for the product encoded by the selectable marker. Many commonly used selectable markers for plant transformation are well known in the transformation art, and include, for example, nucleic acids that code for enzymes that metabolically detoxify a selective chemical agent which may be an antibiotic or an herbicide, or nucleic acids that encode an altered target which is insensitive to the inhibitor. Positive selection methods are also known in the art.

Commonly used selectable markers in plants include, but are not limited to: neomycin phosphotransferase II (nptII) conferring resistance to kanamycin, hygromycin phosphotransferase conferring resistance to the antibiotic hygromycin, bacterial selectable markers that confer resistance to antibiotics (e.g., gentamycin acetyl transferase, streptomycin phosphotransferase, and aminoglycoside-3'-adenyl transferase, selectable markers conferring resistance to herbicides (e.g., glyphosate, glufosinate, or bromoxynil). Selection of transformed plant cells can also be based on screening presumptively transformed plant cells rather than direct genetic selection of transformed cells for resistance to a toxic substance such as an antibiotic; such markers include without limitation alpha-glucuronidase (GUS), alpha-galactosidase, luciferase, and Green Fluorescent Protein (GFP) and mutant GFPs.

Expression Vectors for Plant Transformation—Promoters.

Transgenes included in expression vectors are generally driven by a nucleotide sequence comprising a regulatory element (for example, a promoter). Numerous types of promoters are well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells.

Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in certain tissue are referred to as "tissue-specific." A "cell type" specific promoter preferentially drives expression in certain cell types in one or more organs, for example, vascular cells in roots or leaves. An "inducible" promoter is a promoter that is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

Many suitable promoters are known in the art and can be selected and used to achieve the desired outcome.

Signal Sequences for Targeting Proteins to Subcellular Compartments.

Transport of polypeptides produced by transgenes to a subcellular compartment such as the chloroplast, vacuole, peroxisome, glyoxysome, cell wall, or mitochondrion, or for secretion into the apoplast, is generally accomplished by means of operably linking a nucleotide sequence encoding a signal sequence to the 5' and/or 3' region of a nucleic acid encoding the polypeptide of interest. Signal sequences at the 5' and/or 3' end of the coding sequence target the polypeptide to particular subcellular compartments.

The presence of a signal sequence can direct a polypeptide to either an intracellular organelle or subcellular compartment or for secretion to the apoplast. Many signal sequences are known in the art. See, for example, Becker, et al., Plant Mol. Biol., 20:49 (1992); Close, P. S., Master's Thesis, Iowa State University (1993); Knox, C., et al., "Structure and Organization of Two Divergent Alpha-Amylase Genes from Barley," Plant Mol. Biol., 9:3-17 (1987); Lerner, et al., Plant Physiol., 91:124-129 (1989); Fontes, et al., Plant Cell, 3:483-496 (1991); Matsuoka, et al., PNAS, 88:834 (1991); Gould, et al., J. Cell. Biol., 108:1657 (1989); Creissen, et al., Plant J, 2:129 (1991); Kalderon, et al., A short amino acid sequence able to specify nuclear location, Cell, 39:499-509 (1984); and Steifel, et al., Expression of a maize cell wall hydroxyproline-rich glycoprotein gene in early leaf and root vascular differentiation, Plant Cell, 2:785-793 (1990).

Foreign Polypeptide Transgenes and Agronomic Transgenes.

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign polypeptide then can be extracted from a tissue of interest or from total biomass. Protein extraction from plant biomass can be accomplished by known methods which are discussed, for example, by Heney and Orr, Anal. Biochem., 114:92-6 (1981). According to a representative embodiment, the transgenic plant provided for commercial production of foreign protein is a melon plant of the invention. In another embodiment, the biomass of interest is seed and/or fruit.

Likewise, by means of the present invention, agronomic transgenes and other desired added traits can be expressed in transformed plants (and their progeny, e.g., produced by breeding methods). More particularly, plants can be genetically engineered to express various phenotypes of agronomic interest or other desired added traits. Exemplary nucleic acids of interest in this regard conferring a desired added trait(s) include, but are not limited to, those transgenes that confer resistance to confer resistance to plant pests (e.g., nematode or insect) or disease (e.g., fungal, bacterial or viral), transgenes that confer herbicide tolerance, transgenes that confer male sterility, and transgenes that confer or contribute to a value-added trait such as increased nutrient content (e.g., iron, nitrate), increased sweetness (e.g., by introducing a transgene coding for monellin), modified fatty acid metabolism (for example, by introducing into a plant an antisense sequence directed against stearyl-ACP desaturase to increase stearic acid content of the plant), modified carbohydrate composition (e.g., by introducing into plants a transgene coding for an enzyme that alters the branching pattern of starch), modified fruit color (e.g., external fruit color and/or fruit flesh), or modified flavor profile of the fruit.

In embodiments, the transgene encodes a non-translated RNA (e.g., RNAi) that is expressed to produce targeted inhibition of gene expression, thereby conferring the desired trait on the plant.

In embodiments, the transgene encodes the machinery used for genome editing techniques.

Any transgene, including those exemplified above, can be introduced into the melon plants of the invention through a variety of means including, but not limited to, transformation (e.g., genetic engineering techniques), conventional breeding, and introgression methods to introduce the transgene into other genetic backgrounds.

Methods for Plant Transformation.

Numerous methods for plant transformation have been developed, including biological and physical plant transformation protocols. See, for example, Miki, et al., "Procedures for Introducing Foreign DNA into Plants" in Methods in Plant Molecular Biology and Biotechnology, Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in Methods in Plant Molecular Biology and Biotechnology, Glick and Thompson Eds., CRC Press, Inc., Boca Raton, pp. 89-119 (1993). Commonly used plant transformation methods include *agrobacterium*-mediated transformation and direct transgene transfer methods (e.g., microprojectile-mediated transformation, sonication, liposome or spheroplast fusion, and electroporation of protoplasts or whole cells).

Following transformation of plant target tissues, expression of selectable marker transgenes (e.g., as described above) allows for preferential selection of transformed cells, tissues and/or plants, using regeneration and selection methods now well known in the art.

The foregoing methods for transformation are typically used to produce a transgenic melon line. The transgenic melon line can then be crossed with another (non-transgenic or transgenic) line in order to produce a new transgenic melon line. Alternatively, a transgene that has been engineered into a particular plant using transformation techniques can be introduced into another plant or line using traditional breeding (e.g., backcrossing) techniques that are well known in the plant breeding arts. For example, a backcrossing approach can be used to move an engineered transgene from a public, non-elite inbred line into an elite inbred line, or from an inbred line containing a foreign transgene in its genome into an inbred line or lines which do not contain that transgene. As used herein, "crossing" can refer to a simple X by Y cross, or the process of backcrossing, depending on the context.

Locus Conversion.

When the term "plant" is used in the context of the present invention, this term also includes any locus conversions of that plant or variety. The term "locus converted plant" as used herein refers to those plants that are developed, for example, by backcrossing, genome editing, genetic transformation and/or mutation, wherein essentially all of the desired morphological and physiological characteristics of a variety (e.g., fruits with a firm flesh and/or an extended shelf life) are recovered in addition to the one or more genes introduced into the variety. To illustrate, backcrossing methods can be used with the present invention to improve or introduce a characteristic into the variety. The term "backcrossing" as used herein refers to the repeated crossing of a hybrid progeny back to the recurrent parent, e.g., backcrossing 1, 2, 3, 4, 5, 6, 7, 8, 9, or more times to the recurrent parent. The parental plant that contributes the gene/locus for the desired characteristic is termed the "nonrecurrent" or "donor parent." This terminology refers to the fact that the nonrecurrent parent is generally used one time in the breeding e.g., backcross) protocol and therefore does not recur. The gene/locus that is transferred can be a native gene/locus, a mutated native gene/locus or a transgene introduced by genetic engineering techniques into the plant (or ancestor thereof). The parental plant into which the locus/loci from the nonrecurrent parent are transferred is known as the "recurrent" parent as it is used for multiple rounds in the backcrossing protocol. Poehlman & Sleper (1994) and Fehr (1993). In a typical backcross protocol, the original variety of interest (recurrent parent) is crossed to a second variety (nonrecurrent parent) that carries the locus/loci of interest to be transferred. The resulting progeny from this cross are then crossed again to the recurrent parent and the process is repeated until a plant is obtained wherein essentially all of the desired morphological and physiological characteristics of the recurrent parent are recovered in the converted plant in addition to the transferred locus/loci and associated trait(s) from the nonrecurrent parent.

Genetic Analysis of Cantaloupe Cultivars ME466, ME467, ME468, ME469, ME470 and ME480.

The invention further provides a method of determining a genetic characteristic of cantaloupe cultivars ME466, ME467, ME468, ME469, ME470 and ME480 or a progeny thereof, e.g., a method of determining a genotype of cantaloupe cultivars ME466, ME467, ME468, ME469, ME470 and ME480 or a progeny thereof. In embodiments, the method comprises detecting in the genome of a ME466, ME467, ME468, ME469, ME470 or ME480 plant, or a progeny plant thereof, at least a first polymorphism, e.g., by detecting a nucleic acid marker by a method comprising nucleic acid amplification and/or nucleic acid sequencing. To illustrate, in embodiments, the method comprises obtaining a sample of nucleic acids from the plant and detecting at least a first polymorphism in the nucleic acid sample. Optionally, the method may comprise detecting a plurality of polymorphisms (e.g., two or more, three or more, four or more, five or more, six or more, eight or more or ten or more polymorphisms, etc.) in the genome of the plant. In representative embodiments, the method further comprises storing the results of the step of detecting the polymorphism(s) on a computer readable medium. The invention further provides a computer readable medium produced by such a method.

DEPOSIT

Applicants have made a deposit of at least 2500 seeds of cantaloupe cultivars ME466, ME467, ME468, ME469, ME470 and ME480 with the American Type Culture Collection (ATCC), 10801 University Boulevard, Manassas, Va., 20110-2209 U.S.A. under ATCC Deposit Nos. PTA-126773, PTA-126774, PTA-126775, PTA-126776, PTA-126777 and PTA-126778, respectively. These deposits will be maintained in the ATCC depository, which is a public depository, for a period of 30 years, or 5 years after the most recent request, or for the effective life of the patent, whichever is longer, and will be replaced if any of the deposited seed becomes nonviable during that period. Additionally, Applicants have satisfied all the requirements of 37 C.F.R. §§ 1.801-1.809, including providing an indication of the viability of the samples. During the pendency of this application, access to the deposited material will be afforded to the Commissioner on request. All restrictions on the availability of the deposited material from the ATCC to the public will be irrevocably removed upon granting of the patent. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Variety Protection Act (7 USC § 2321 et seq.).

Access to this deposits will be available during the pendency of this application to persons determined by the Commissioner of Patents and Trademarks to be entitled thereto under 37 C.F.R. § 1.14 and 35 U.S.C. § 122. Upon allowance of any claims in this application directed to a variety, all restrictions on the availability to the public of that variety will be irrevocably removed by affording access to a deposit of at least 2500 seeds of the same variety with the American Type Culture Collection, 10801 University Boulevard, Manassas, Va. 20110-2209 U.S.A.

The foregoing invention has been described in detail by way of illustration and example for purposes of clarity and understanding. However, it will be apparent that certain changes and modifications such as single locus modifications and mutations, somaclonal variants, variant individuals selected from large populations of the plants of the instant inbred and the like may be practiced within the scope of the invention. Thus, although the foregoing invention has been described in some detail in this document, it will be obvious that changes and modifications may be practiced within the scope of the invention.

What is claimed is:

1. A seed of a plant selected from cantaloupe cultivar ME466, ME467, ME468, ME469, ME470 or ME480, a representative sample of seed having been deposited under ATCC Accession Nos. PTA-126773, PTA-126774, PTA-126775, PTA-126776, PTA-126777 and PTA-126778, respectively.

2. A plant of cantaloupe cultivar ME466, ME467, ME468, ME469, ME470 or ME480 grown from the seed of claim 1 when grown under the same environmental conditions.

3. A cantaloupe plant having all the physiological and morphological characteristics of the plant of claim 2.

4. A seed that produces the plant of claim 3.

5. A progeny melon plant comprising at least one set of chromosomes of the plant of claim 2, wherein the plant of claim 2 is cantaloupe cultivar ME466, ME467 or ME468.

6. An F1 seed of the plant of claim 2, wherein the plant of claim 2 is cantaloupe cultivar ME466, ME467 or ME468.

7. A plant part of the plant of claim 2, wherein the plant part is a fruit, fruit flesh, a scion, a rootstock, a shoot, an anther, pollen, an ovule, a root, a leaf, or a cell.

8. A tissue culture of regenerable cells of the plant of claim 2.

9. A plant regenerated from the tissue culture of regenerable cells of claim 8, wherein the regenerated plant comprises all of the physiological and morphological characteristics of the plant of claim 2.

10. A converted melon plant produced by introducing a single locus conversation into the plant of claim 2, which is cantaloupe cultivar ME466, ME467 or ME468, wherein said converted melon plant comprises said single locus conversion and otherwise comprises all of the physiological and morphological characteristics of cantaloupe cultivar ME466, ME467 or ME468.

11. A seed that produces the plant of claim 10.

12. A method of producing melon seed, the method comprising crossing the plant of claim 2 with itself or a second melon plant and harvesting the resulting seed.

13. An F1 melon seed produced by the method of claim 12, wherein the plant to be crossed is cantaloupe cultivar ME466, ME467 or ME468.

14. A melon plant, or part thereof which is a fruit, fruit flesh, a scion, a rootstock, a shoot, an anther, pollen, an ovule, a root, a lear, or a cell, produced by growing the seed of claim 13.

15. A method of developing a melon line in a melon plant breeding program using plant breeding techniques, which include employing a melon plant, or its parts, as a source of plant breeding material, the method comprising:
    (a) obtaining the cantaloupe plant, or parts thereof, of claim 2 as a source of breeding material; and
    (b) applying plant breeding techniques.

16. A method for producing a seed of a melon plant derived from the plant of claim 2, the method comprising:
    (a) crossing a melon plant of cantaloupe cultivar ME466, ME467, ME468, ME469, ME470 or ME480 with a second melon plant;
    (b) allowing seed to form;
    (c) growing a plant from the seed of step (b) to produce a plant derived from cantaloupe cultivar ME466, ME467, ME468, ME469, ME470 or ME480;
    (d) selfing the plant of step (c) or crossing it to a second melon plant to form additional melon seed derived from cantaloupe cultivar ME466, ME467, ME468, ME469, ME470 or ME480; and
    (e) optionally repeating steps (c) and (d) one or more times to generate further derived melon seed from melon cultivar ME466, ME467, ME468, ME469, ME470 or ME480, wherein in step (c) a plant is grown from the additional melon seed of step (d) in place of growing a plant from the seed of step (b).

17. A method of producing cantaloupe fruit, the method comprising:
    (a) growing the plant of claim 2 to produce a cantaloupe fruit; and
    (b) harvesting the cantaloupe fruit from the plant.

18. A method of vegetatively propagating the plant of claim 2, the method comprising:
    (a) collecting tissue capable of being propagated from a plant of cantaloupe cultivar ME466, ME467, ME468, ME469, ME470 or ME480, respectively;
    (b) cultivating the tissue to obtain proliferated shoots; and
    (c) rooting a proliferated shoot to obtain a rooted plantlet.

19. The method of claim 18, further comprising growing a plant from the rooted plantlet.

20. A plant obtained by the method of claim 19, wherein the plant comprises all of the physiological and morphological characteristics of cantaloupe cultivar ME466, ME467, ME468, ME468, ME470 or ME480, respectively.

21. A method of introducing a desired added trait into cantaloupe cultivar ME466, ME467 or ME468, the method comprising:
    (a) crossing the plant of claim 2, which is ME466, ME467 or ME468, with a melon plant that comprises a desired added trait to produce F1 progeny;
    (b) selecting an F1 progeny that comprises the desired added trait;
    (c) backcrossing the selected F1 progeny with the same cantaloupe cultivar as in step (a) to produce backcross progeny;
    (d) selecting backcross progeny comprising the desired added trait; and
    (e) repeating steps (c) and (d) one or more times to produce a plant derived from cantaloupe cultivar ME466, ME467 or ME468 comprising a desired added trait and essentially all of the physiological and morphological characteristics of cantaloupe cultivar ME466, ME467 or ME468, wherein the selected backcross progeny produced in step (d) is used in place of the selected F1 progeny in step (c).

22. A melon plant produced by the method of claim 21 or a selfed progeny thereof, wherein the melon plant has the desired added trait and otherwise has all the physiological and morphological characteristics of cantaloupe cultivar ME466, ME467 or ME468.

23. A seed of the plant of claim 22, wherein the seed produces a plant that has the desired added trait.

24. A seed that produces the plant of claim 22.

25. A method of producing a plant of cantaloupe cultivar ME466, ME467, ME468, ME469, ME470 or ME480 comprising a desired added trait, the method comprising introducing a transgene conferring the desired added trait into the plant of claim 2.

26. A melon plant produced by the method of claim 25 or a selfed progeny thereof, wherein the melon plant has the desired added trait and otherwise all of the physiological and morphological characteristics of cantaloupe cultivar ME466, ME467, ME468, ME469, ME470 or ME480, respectively.

27. A seed that produces the plant of claim 26.

28. A method for producing a seed from the plant of claim 2, wherein the plant is cantaloupe cultivar ME469, ME470 or ME480, the method comprising selfing a melon plant of cantaloupe cultivar ME469, ME470 or ME480 for one or more generations and allowing seed to form.

29. A method of determining a genotype of cantaloupe cultivar ME466, ME467, ME468, ME469, ME470 or ME480, the method comprising:
    (a) obtaining a sample of nucleic acids from the plant of claim 2; and
    (b) detecting a polymorphism in the nucleic acid sample using molecular biology techniques.

30. A plant, plant part, or F1 seed of cantaloupe cultivar ME466.

31. A plant, plant part, or F1 seed of cantaloupe cultivar ME467.

32. A plant, plant part, or F1 seed of cantaloupe cultivar ME468.

33. A plant of cantaloupe cultivar ME469, or a seed that produces cantaloupe cultivar ME469, or a plant part of cantaloupe cultivar ME469 which is a fruit, fruit flesh, a scion, a rootstock, a shoot, an anther, pollen, an ovule, a root, or a leaf.

34. A plant of cantaloupe cultivar ME470, or a seed that produces cantaloupe cultivar ME470, or a plant part of cantaloupe cultivar ME470 which is fruit, fruit flesh, a scion, a rootstock, a shoot, an anther, pollen, an ovule, a root, or a leaf.

35. A plant of cantaloupe cultivar ME480, or a seed that produces cantaloupe cultivar ME480, or a plant part of cantaloupe cultivar ME480 which is a fruit, fruit flesh, a scion, a rootstock, a shoot, an anther, pollen, an ovule, a root, or a leaf.

* * * * *